United States Patent [19]

Lord

[11] Patent Number: 5,089,527

[45] Date of Patent: Feb. 18, 1992

[54] PENTAMIDINE SOLUTIONS

[75] Inventor: John D. Lord, London, England

[73] Assignee: Rhone-Poulenc Sante, Antony Cedex, France

[21] Appl. No.: 478,488

[22] Filed: Feb. 12, 1990

[30] Foreign Application Priority Data

Feb. 15, 1989 [GB] United Kingdom ............ 8903438
Oct. 9, 1989 [GB] United Kingdom ............ 8922707

[51] Int. Cl.$^5$ ........................................... A61K 31/155
[52] U.S. Cl. ................................. 514/636; 514/970
[58] Field of Search ........................................ 514/636

[56] References Cited

U.S. PATENT DOCUMENTS 4,853,416  8/1989  Anaebonam et al. ............ 514/636

Primary Examiner—Leonard Schenkman
Attorney, Agent, or Firm—Morgan & Finnegan

[57] ABSTRACT

The invention provides a stabilized aqueous solution of a water soluble pentamidine salt comprising an acetate buffer, and having a total acetate concentration of 0.01–0.06M, and a pH of 4.0–5.0 at room temperature.

12 Claims, No Drawings

5,089,527

PENTAMIDINE SOLUTIONS

FIELD OF THE INVENTION

This invention relates to a stabilized aqueous solution of a pentamidine salt, for example the isethionate, which is particularly suitable for use in a nebulizer, and a process for its production.

BACKGROUND OF THE INVENTION

Pentamidine [1,5-bis(4-amidinophenoxy)pentane] is a trypanocidal compound which is particularly active against Leishmaniasis. It unfortunately suffers from a large number of side-effects and has now been substantially displaced by other drugs. However, it is also active against pneumocystis carinii pneumonia (PCP)—one of the commonest, lethal, opportunistic infections suffered by AIDS patents—having utility as both a curative and prophylactic agent.

Due to the instability of aqueous pentamidine solutions, the material is normally supplied in the form of its isethionate (2-hydroxyethanesulphonate), as a powdered material to be reconstituted with water immediately prior to administration by injection or infusion. This means that the patient still suffers from the side effects. Although these are more acceptable in the treatment of a potentially lethal infection, it is nevertheless desirable to overcome them if at all possible. With this in mind it is clearly advantageous to administer the drug directly to the site of infection, i.e. to the lungs.

Therefore pentamidine isethionate is now used in solution in nebulizers for administration by inhalation. Not only does this result in direct treatment of the infected site, but also absorption from the lungs is relatively limited, so that the side effects are substantially reduced.

Because of the abovementioned instability in solution it is still necessary to supply the material in the form of an ampouled solid, which is dissolved in water before use. This is a relatively troublesome process and involves the use of needles and syringes (clearly undesirable for many AIDS patients). It would therefore be highly desirable to produce pentamidine in a stabilized solution form, which can be placed directly into a nebulizer when required for use.

It has been found that pentamidine is more stable in acidic than in alkaline aqueous media. However the production of usable solutions appeared to be impossible as heretofore pentamidine has been found to be insoluble in, or precipitated or salted out by, buffer solutions which are also pharmaceutically and pharmacologically acceptable at concentrations normally used. This was not unexpected in view of the known difficulty of solublizing pentamidine and the need to use unusual anions such as isethionate when a water soluble form of pentamidine was required.

DESCRIPTION OF THE INVENTION

We have, however, found that the use of a dilute acetate buffer does allow the formation of a stabilized solution of water soluble pentamidine salts, such as the mesylate (methanesulphonate), gluconate, lactate or isethionate.

The present invention accordingly provides an aqueous solution of a water soluble pentamidine salt, e.g. the mesylate, gluconate, lactate or, preferably, isethionate comprising an acetate buffer, and having a total acetate concentration of 0.01–0.06M, preferably 0.02M, and a pH of 4.0–5.0 at room temperature, the solution preferably being sterile. The preferred pH is about 4.6.

The solution can be made up by mixing preformed solutions or by direct dissolution of the solid in the buffer and can be sterilized by, for example, filtration through a bacteria-retaining filter.

The buffer is of conventional form, comprising an aqueous solution of acetic acid and a pharmaceutically acceptable acetate salt, e.g. an alkali metal, such as sodium or potassium, acetate or ammonium acetate in the correct proportions for the establishment of the required pH. Sodium acetate is preferred.

Typically the buffer has an initial pH of 4.6 to 5.0 and is 0.1 M in acetate and when the solution is made up this is diluted by a factor of 2 to 10, preferably about 5, to give the final acetate concentration.

The water soluble pentamidine salts used in the invention preferably have a solubility greater than about 40 mg/ml in water at ambient temperature.

The maximum pentamidine salt, e.g. isethionate, concentration achievable in compositions according to the invention varies depending upon the acetate concentration used. In 0.04M acetate, the maximum concentration of pentamidine salt, e.g. isethionate, is about 6% w/v, whereas when the acetate concentration is reduced to 0.02M, then up to about a 10% w/v loading of pentamidine salt, e.g. isethionate, (equivalent to its saturation solubility in water) can be reached. The pentamidine salt concentration will generally be from 1% w/v to 10% w/v and preferably from 1.2% w/v to 6% w/v.

As the solution is intended for pulmonary administration it is desirable to make it isotonic in order to avoid bronchoconstriction. It is also believed that isotonicity limits droplet size alteration during nebulization and this would clearly be of assistance in controlling the administration.

Normal tonicity adjusting agents such as sodium chloride are unsuitable, just as most ionic species cannot be used in the stabilizing buffer. We have however found that non-ionic tonicity adjusting agents, such as sugars and sugar alcohols can be used and it is particularly preferred to use dextrose, glucose, sorbitol, mannitol or xylitol.

The invention also provides a method for the treatment of a human patient suffering from, or susceptible to, pneumocystis carinii pneumonia which comprises administering to the patient by inhalation as an aerosol, an effective amount of an aqueous solution according to the invention.

In prophylactic treatment typical dosages vary from 30 mg to 600 mg of pentamidine isethionate and the frequency of administration from monthly to thrice weekly (although on occasion only a single dose is given). The preferred dose is 300 mg of pentamidine isethionate every four weeks or 150 mg every fortnight.

In the treatment of an existing infection typical dosages vary from 300 mg to 1000 mg of pentamidine isethionate and the frequency of administration from thrice weekly to daily, typically for up to three weeks or until the infection is successfully treated. The preferred dosage is 600 mg daily.

If a water soluble salt other than the isethionate is used, the amount administered should be such as to provide an equivalent amount of the pentamidine base.

It will be understood that the foregoing doses are typical or preferred. As the administration of pentamidine by inhalation is known, suitable doses for individual patients will be known to, or readily determinable by, those skilled in the art.

The invention also provides an aqueous solution of a water soluble pentamidine salt, e.g. the mesylate, gluconate, lactate or, preferably, isethionate comprising an acetate buffer, and having a total acetate concentration of 0.01-0.06M, preferably 0.02M, and a pH of 4.0-5.0, preferably about 4.6, at room temperature, and preferably being sterile, for use as a medicament in the treatment of pneumocystis carinii pneumonia as hereinbefore described.

EXAMPLES

The following Examples illustrate the invention.

In storage stability tests the relative humidity, unless otherwise specified, is ambient relative humidity.

EXAMPLE 1

A solution was made up from:

| | |
|---|---|
| Pentamidine isethionate | 300 parts by weight |
| Dextrose monohydrate | 80 parts by weight |
| *0.1M acetate buffer (pH 4.6) | 1000 parts by weight |
| Demineralized water | 4000 parts by weight |

*containing 0.292% v/v acetic acid and 0.667% w/v sodium acetate

This was filled through a 0.45 μm filter into sterile ampoules and had an initial pH of 4.57 and an initial measured pentamidine isethionate content of 55.3 mg/ml.

The following stability data were obtained:

| Storage period (months) | Storage conditions | | | | | | | |
|---|---|---|---|---|---|---|---|---|
| | 22° C./ 55% R.H. | | 30° C. | | 37° C. | | 45° C. | |
| | pH | P.I. | pH | P.I. | pH | P.I. | pH | P.I. |
| 1 | 4.61 | 55.5 | 4.50 | 55.7 | 4.45 | 55.0 | 4.47 | 55.5 |
| 2 | 4.48 | 55.4 | 4.47 | 55.1 | 4.47 | 55.4 | 4.48 | 56.7 |
| 3 | 4.48 | 55.5 | 4.48 | 56.2 | 4.48 | 56.7 | 4.48 | 57.2 |
| 7 | 4.71 | 56.2 | 4.78 | 57.2 | 4.76 | 57.5 | — | — |
| 11.5 | 4.53 | 55.6 | 4.56 | 57.8 | 4.51 | 59.2 | — | — |

R.H. = relative humidity
P.I. = concentration of pentamidine isethionate in mg/ml

EXAMPLE 2

In a similar manner to that of Example 1, a solution was made up from:

| | |
|---|---|
| Pentamidine isethionate | 60 parts by weight |
| Dextrose monohydrate | 240 parts by weight |
| 0.1M acetate buffer (pH 4.6) (as in Example 1) | 1000 parts by weight |
| Sterile Water | 4000 parts by weight |

This was sterilized by being passed through a 0.22 μm filter and filled into sterile vials.

EXAMPLE 3

A solution was made up consisting of:

| | |
|---|---|
| Pentamidine isethionate | 5.58% w/w |
| Glucose B.P. | 1.49% w/w |
| Acetate buffer solution (as in Example 1) | 18.58% w/w |
| Water for injections | 74.35% w/w |

5 ml samples of this solution [nominal content of pentamidine isethionate of 300 mg (58 mg/ml—measured initial content 58.0 mg/ml)] were stored in low density polyethylene bottles and glass vials.

The following stability data were obtained:

| Storage period (months) | Storage conditions | | | | | |
|---|---|---|---|---|---|---|
| | 22° C./55% R.H. | | 30° C. | | 37° C. | |
| | pH | P.I. | pH | P.I. | pH | P.I. |
| 1 | 4.63 | 57.1 | 4.58 | 57.0 | 4.61 | 57.6 |
| 3 | 4.63 | 57.7 | 4.62 | — | 4.58 | 57.3 |
| 6 | 4.64 | 57.4 | 4.55 | 58.0 | 4.55 | 58.8 |

EXAMPLE 4

A solution was made up consisting of:

| | |
|---|---|
| Pentamidine isethionate | 1.13% w/w |
| Glucose B.P. | 4.62% w/w |
| Acetate buffer solution (as in Example 1) | 18.85% w/w |
| Water for injections | 75.40% w/w |

The solution pH was again 4.60.

5 ml samples of this solution [nominal content of pentamidine isethionate of 60 mg (12 mg/ml—measured initial content 11.8 mg/ml)] were placed in low density polyethylene bottles and glass vials.

The following stability data were obtained:

| Storage period (months) | Storage conditions | | | | | |
|---|---|---|---|---|---|---|
| | 22° C./55% R.H. | | 30° C. | | 37° C. | |
| | pH | P.I. | pH | P.I. | pH | P.I. |
| 1 | 4.60 | 11.6 | 4.60 | 11.6 | 4.61 | 11.7 |
| 3 | 4.58 | 11.4 | 4.57 | — | 4.56 | 11.7 |
| 6 | 4.61 | 11.7 | 4.62 | 11.9 | 4.60 | 11.9 |

COMPARISON EXAMPLE 1

A mixture was made up consisting of:

| | |
|---|---|
| Pentamidine isethionate | 300 mg |
| #Sodium chloride | 10 mg |
| Demineralized water | 5 ml |

(#theoretically sufficient for isotonicity).

This resulted in an immediate precipitate. The pH of the mixture was 5.86.

COMPARISON EXAMPLE 2

A mixture was made up consisting of:

| | |
|---|---|
| Pentamidine isethionate | 300 mg |
| +Sodium citrate | 0.397 mg |
| +Citric acid | 0.221 mg |
| Demineralized water | 5 ml |

(+equivalent to a 100-fold dilution of a conventional pH 4.6 buffer and approximately 0.54 mM in citrate).

A heavy precipitate formed and it was impossible to measure the pH of the mixture.

COMPARISON EXAMPLE 3

A mixture was made up consisting of:

| | |
|---|---|
| Pentamidine isethionate | 300 mg |
| Demineralized water | 5 ml |
| 0.1M HCl q.s. | pH 4.6 |

This was compared with a solution according to the invention, consisting of:

| | |
|---|---|
| Pentamidine isethionate | 300 mg |
| 0.1M acetate buffer (as used in Example 1) | 1 ml |
| Demineralized water | 4 ml |

(which had an initial pH of 4.31) in an accelerated stability test.

After 84 hours at 60° C. the comparison solution showed 2.1% decomposition and a pH of 6.3, whereas the solution according to the invention showed only 0.2% decomposition and a pH of 4.17.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

I claim:

1. An aqueous solution of a water soluble pentamidine salt comprising an acetate buffer, and having a total acetate concentration of 0.01–0.06M, a pentamidine salt concentration from 1% w/v to 10% w/v, and a pH of about 4.6 at room temperature.

2. A solution according to claim 1 wherein the water soluble pentamidine salt is the mesylate, gluconate, lactate or isethionate.

3. A solution according to claim 1 wherein the water soluble pentamidine salt is the isethionate.

4. A solution according to any one of the preceding claims wherein the total acetate concentration is 0.02M.

5. A solution according to claim 1 which is sterile.

6. A solution according to claim 1, wherein the buffer comprises an aqueous solution of acetic acid and an alkali metal acetate or ammonium acetate.

7. A solution according to claim 1, wherein the buffer comprises an aqueous solution of acetic acid and sodium acetate.

8. A solution according to claim 1, wherein the pentamidine salt concentration is from 1.2% w/v to 6% w/v.

9. A solution according to claim 1 which is isotonic.

10. A solution according to claim 9, comprising as a non-ionic tonicity adjusting agent, a sugar or sugar alcohol.

11. A solution according to claim 10 wherein the sugar or sugar alcohol is dextrose, glucose, sorbitol, mannitol or xylitol.

12. A method for the treatment of a human patient suffering from, or susceptible to, Pneumocystis carinii pneumonia comprising administering to the patient by inhalation as an aerosol, an effective amount of an aqueous solution according to claim 1.

* * * * *